(12) United States Patent
Ohara et al.

(10) Patent No.: US 9,993,493 B2
(45) Date of Patent: Jun. 12, 2018

(54) COMPOSITION FOR PREVENTION, AMELIORATION OR TREATMENT OF METABOLIC SYNDROME

(71) Applicant: HOUSE WELLNESS FOODS CORPORATION, Hyogo (JP)

(72) Inventors: Tatsuya Ohara, Hyogo (JP); Koutarou Muroyama, Hyogo (JP); Shinji Murosaki, Nara (JP); Yoshihiro Yamamoto, Hyogo (JP)

(73) Assignee: HOUSE WELLNESS FOODS CORPORATION, Hyogo (JP)

( * ) Notice: Subject to any disclaimer, the term of this patent is extended or adjusted under 35 U.S.C. 154(b) by 218 days.

(21) Appl. No.: 14/733,592

(22) Filed: Jun. 8, 2015

(65) Prior Publication Data
US 2015/0265645 A1 Sep. 24, 2015

Related U.S. Application Data

(63) Continuation of application No. 13/261,527, filed as application No. PCT/JP2011/050495 on Jan. 14, 2011, now abandoned.

(30) Foreign Application Priority Data

May 24, 2010 (JP) ................................. 2010-118051

(51) Int. Cl.
| | |
|---|---|
| *A61K 31/7048* | (2006.01) |
| *A61K 31/522* | (2006.01) |
| *A61K 31/765* | (2006.01) |
| *A61K 31/375* | (2006.01) |
| *A61K 31/352* | (2006.01) |
| *A23L 33/00* | (2016.01) |
| *A23L 33/10* | (2016.01) |
| *A61K 9/20* | (2006.01) |

(52) U.S. Cl.
CPC .......... *A61K 31/7048* (2013.01); *A23L 33/10* (2016.08); *A23L 33/30* (2016.08); *A61K 31/352* (2013.01); *A61K 31/375* (2013.01); *A61K 31/522* (2013.01); *A61K 31/765* (2013.01); *A23V 2002/00* (2013.01); *A61K 9/2018* (2013.01); *A61K 9/2054* (2013.01)

(58) Field of Classification Search
None
See application file for complete search history.

(56) References Cited

U.S. PATENT DOCUMENTS

| | | | | |
|---|---|---|---|---|
| 2010/0166851 | A1* | 7/2010 | Dallas .................. | A61K 31/375 424/451 |
| 2010/0273727 | A1* | 10/2010 | Mukai .................. | A61K 31/045 514/27 |

FOREIGN PATENT DOCUMENTS

| | | |
|---|---|---|
| JP | H11100325 A | 4/1999 |
| JP | 2003-034636 A | 2/2003 |
| JP | 2004-035417 A | 2/2004 |
| JP | 2005-047839 A | 2/2005 |
| JP | 2008156341 A | 7/2008 |
| JP | 2008291002 A | 12/2008 |
| JP | 2009-055905 A | 3/2009 |
| WO | WO-2006067866 A1 | 6/2006 |
| WO | WO-2008143182 A1 | 11/2008 |

OTHER PUBLICATIONS

Kanaze, F. I., Gabrieli, C., Kokkalou, E., Georgarakis, M., & Niopas, I. (2003). Simultaneous reversed-phase high-performance liquid chromatographic method for the determination of diosmin, hesperidin and naringin in different citrus fruit juices and pharmaceutical formulations. Journal of pharmaceutical and biomedical analysis, 33(2), 243-249.*

Grundy, S. M., Brewer, H. B., Cleeman, J. I., Smith, S. C., & Lenfant, C. (2004). Definition of metabolic syndrome. Circulation, 109(3), 433-438. (Year: 2004).*

International Search Report in corresponding PCT/JP2011/050495 dated Mar. 1, 2011.

Mitsuzumi et al., "Serum triglyceride lowering effect and its mechanism of glucosyl hesperidin," Proceedings of the 63rd Annual Meeting of the Japanese Society of Nutrition and Food Science, p. 205 (2005).

Sakurai et al., "Antioxidative Effects of a New Lychee Fruit-Derived Polyphenol Mixture, Oligonol, Converted into a Low-Molecular Form in Adipocytes," Biosci. Biotechnol. Biochem. 72(2), pp. 463-376 (2008).

Nishihira et al., "Amelioration of abdominal obesity by low-molecular-weight polyphenol (Olignol) from lychee," J. Functional Foods, vol. 1, pp. 341-348 (2009).

Dodd et al., "Caffeine and Exercise Prformance," Sports Medicine 15(1): pp. 14-23 (1993).

Dulloo et al., "Normal caffeine consumption: influence on thermogenesis and daily energy expenditure in lean and postobese human volunteers," Am. J. Clin. Nutr. 49, pp. 44-50 (1989).

(Continued)

Primary Examiner — James H Alstrum-Acevedo
Assistant Examiner — Dale R Miller
(74) Attorney, Agent, or Firm — Marshall, Gerstein & Borun LLP (57) ABSTRACT

A composition comprising (a) and (b), and a food or drink or a medicine comprising the composition, wherein
(a) is at least a kind of polyphenols selected from the group consisting of a polyphenol containing 15 mass % or more of proanthocyanidin having a polymerization degree of 1 to 3, hesperidin, a hesperidin derivative, and hesperetin; and
(b) is at least a kind of xanthine derivatives, the mass ratio of (a):(b) in the composition being 1:(0.001 to 5), are useful for the prevention, amelioration, or treatment of metabolic syndrome, disorders of lipid metabolism (for example, fatty liver, hyperlipidemia), obesity (for example, visceral fat accumulation, subcutaneous fat accumulation), or the like.

2 Claims, 6 Drawing Sheets

(56) References Cited

OTHER PUBLICATIONS

Hollands et al., "A simple apparatus for comparative measurements of energy expenditure in human subjects: the thermic effect of caffeine," *Am. J. Clin. Nutr.* 34, pp. 2291-2294 (1981).
Hanawa et al., "Effect of Intake of the Tablet Containing Glucosyl Hesperidin on Body Weight and Serum Triglyceride Levels in Humans," *Jpn Pharmacol Ther* 36(12), pp. 1141-1158 (2008).
Written Opinion in coresponding PCT/JP2011/050495 dated Feb. 22, 2011.
International Preliminary Report on Patentability in corresponding PCT/JP2011/050495 dated Dec. 10, 2012.
Definition of "prevention" from the Institute for International Medical Education [online], [Retrieved on Mar. 24, 2011]. Retrieved from the Internet <http://www.iime.org/glossary.htm>. Published Feb. 2002, p. 1, 2, 26, 27 and 29.
Maureen Rouhi, A. (2004) Metabolic Syndrome. Chemical & Engineering News, vol. 82, No. 47, p. 83-99.

\* cited by examiner

COMPOSITION FOR PREVENTION, AMELIORATION OR TREATMENT OF METABOLIC SYNDROME

CROSS-REFERENCE TO RELATED APPLICATIONS

This application claims the priority benefit of U.S. application Ser. No. 13/261,527 filed Nov. 26, 2012 which is a U.S. National Stage of PCT/JP2011/050495 filed Jan. 14, 2011 which claims priority to JP 2010-118051 filed May 24, 2010, the disclosures of which are incorporated herein by reference in their entireties.

TECHNICAL FIELD

The present invention relates to a composition for the prevention, amelioration, or treatment of metabolic syndrome. More specifically, the present invention relates to a composition comprising a polyphenol and a xanthine derivative, for the prevention, amelioration, or treatment of metabolic syndrome.

BACKGROUND ART

In recent years, with steadily increasing obesity, the World Health Organization (WHO) is warning countries around the world of an increased risk of lifestyle-related diseases, which are associated with obesity and include diabetes, hyperlipidemia, hypertension, arteriosclerosis, and fatty liver. Metabolic syndrome is a condition with, in addition to visceral fat accumulation, a combination of risk factors for arteriosclerosis, such as disorders of carbohydrate metabolism (abnormal glucose tolerance, diabetes), disorders of lipid metabolism (hypertriglyceridemia, hypercholesterolemia, and low levels of HDL cholesterol), and hypertension. Even if each of abnormalities (for example, in blood sugar or blood pressure) is mild and at the level of "Care Required" as a result of medical examination or the like, overlapping of such abnormalities tends to cause cardiovascular diseases. It is said that a human having 2 risk factors selected from obesity, hypertension, hyperglycemia, hypertriglyceridemia, and hypercholesterolemia is at the risk of cardiovascular diseases 10 times higher, and a human having 3 to 4 of such risk factors is at the risk 31 times higher than that of a human not having any of such risk factors.

The co-occurrence of obesity, diabetes, hypertension, and hyperlipidemia increases the risk of developing myocardial infarction or cerebral infarction, and therefore is called "Deadly Quartet". Accumulation of visceral fat is considered to be the underlying cause eventually resulting in cardiovascular diseases, such as myocardial infarction and cerebral infarction. Therefore, for the prevention or amelioration of metabolic syndrome and also cardiovascular diseases, decreasing the accumulated visceral fat is important. Since obesity is caused by an imbalance between energy intake and expenditure, it is important, for the purpose of inhibiting obesity, to not only decrease energy intake but also increase energy consumption in basal metabolism or activity metabolism. For decreasing energy intake, low-energy replacements for fat and sugar are provided, but the taste or processability thereof in terms of food is not necessarily satisfactory.

Various measures have been proposed for the prevention of obesity. In recent years, in different kinds of food we regularly take, components having an effect of improving lipid metabolism, or preventing or ameliorating obesity have been found, and are expected to be useful for the prevention of obesity. The inventors focused attention on, among food components having such an effect, hesperidin, a low-molecular proanthocyanidin, and caffeine, which are known to have different working mechanisms with each other. Hesperidin is considered to have an effect of suppressing gene expression of fatty acid synthetase, an effect of increasing gene expression of carnitine palmitoyltransferases I and II, or the like, and thus to promote lipid metabolism (Non Patent Literature 1). Furthermore, it is reported that hesperidin and glucosyl hesperidin have an effect of reducing visceral fat or a waist size (Patent Literature 1). Low-molecular proanthocyanidins are known to have an effect of preventing or improving dysregulated production of adipocytokine and a thermogenic effect by inducing gene expression of uncoupling protein 1 (UCP1) (Non Patent Literature 2). Furthermore, they are known to have an effect of reducing body weight, abdominal circumference, visceral fat, and the like (Non Patent Literature 3). Caffeine is known to have an antagonist effect on adenosine receptors (Non Patent Literature 4), an effect of increasing circulating catecholamine level, and an effect of inhibiting phosphodiesterase activity, which activities facilitate lipid metabolism (Non Patent Literature 5), to inhibit hepatic lipogenesis, and to increase resting metabolic rate and energy consumption, resulting in decrease in body fat and body weight (Non Patent Literature 6). Thus, it is publicly known that each component by itself acts on lipid metabolism. However, there has been no report with regard to combining the components.

CITATION LIST

Patent Literature

Patent Literature 1: JP 2008-156341 A

Non Patent Literature

Non Patent Literature 1:
Proceedings of the 63rd of the Annual Meeting of the Japanese Society of Nutrition and Food Science, 2005, 205
Non Patent Literature 2:
Sakurai et al., Bioscience, Biotechnology, and Biochemistry, 2008, Vol. 72, 463-476
Non Patent Literature 3:
Nishihira et al., J. Functional Foods, Vol. 1, 2009, 341-348
Non Patent Literature 4:
Dodd et al., Sports Med., 1993, Vol. 15, 14-23
Non Patent Literature 5:
Dullo et al., Am. J. Clin. Nutr., 1989, Vol. 49, 44-50
Non Patent Literature 6:
Hollands et al., Am. J. Clin. Nutr., 1981, Vol. 34, 2291-2294

SUMMARY OF INVENTION

Technical Problem

In order to prevent or decrease obesity, dietary therapy based on restricted calorie intake, exercise therapy, and medicinal therapy by use of an anorexiant, etc. are carried out. However, dietary therapy, which often involves excessively restricted diet, requires complicated calorie calculation and strong will, and therefore is difficult for an individual to manage for a long period of time. Also, exercise therapy, which is associated with mental and physical pain, is very difficult to continue for a long period of time in this busy modern society. It is effective to try to consume as much body fat as possible as energy source during exercise, but people with a tendency to become obese have slow fat metabolism, and it is difficult for them to decrease body fat by exercise. Accordingly, development of a composition that can contribute to the prevention or amelioration of obesity by inhibiting hepatic lipogenesis, facilitating resolution of fat accumulated in fat cells, and effectively burning fat, and so has development of a food or drink or a medicine comprising the composition.

The present invention was made in the light of the above-mentioned problems, and an objective of the invention is to provide a composition for the prevention, amelioration, or treatment of metabolic syndrome, disorders of lipid metabolism (for example, fatty liver, hyperlipidemia), obesity (for example, visceral fat accumulation, subcutaneous fat accumulation), or the like, and a food or drink or a medicine comprising the composition.

Solution to Problem

After intensive investigations into compositions which effectively decrease body fat, the present inventors found that a composition comprising hesperidin or a derivative thereof and caffeine, or a composition comprising a low-molecular proanthocyanidin and caffeine has an anti-obesity effect which is surprisingly stronger than the effect exhibited when each of the components is used alone. The inventors have carried out further investigations and completed the present invention.

That is, the present invention relates to the following.
[1] A composition for the prevention, amelioration, or treatment of metabolic syndrome, the composition comprising (a) and (b):
(a) at least a kind of polyphenols selected from the group consisting of a polyphenol containing 15 mass % or more of proanthocyanidin having a polymerization degree of 1 to 3, hesperidin, a hesperidin derivative, and hesperetin; and
(b) at least a kind of xanthine derivatives, the mass ratio of (a):(b) in the composition being 1:(0.001 to 5).
[2] The composition according to the above [1], wherein the mass ratio of (a):(b) is 1:(0.01 to 0.5).
[3] The composition according to the above [1] or [2], wherein the xanthine derivative is caffeine, theophylline, or theobromine.
[4] A medicine, a food or drink, or a feed comprising the composition according to any of the above [1] to [3].
[5] A food or drink comprising the composition according to any of the above [1] to [3], the food or drink being labeled as at least one selected from the group consisting of improving lipid metabolism; promoting basal metabolism; reducing body weight; reducing visceral fat or subcutaneous fat; having a slimming effect; preventing or treating obesity, or ameliorating a symptom thereof; and preventing or treating metabolic syndrome, or ameliorating a symptom thereof.
[6] A method for the prevention, amelioration, or treatment of metabolic syndrome, the method comprising the step of administering an effective amount of a composition comprising (a) and (b):
(a) at least a kind of polyphenols selected from the group consisting of a polyphenol containing 15 mass % or more of proanthocyanidin having a polymerization degree of 1 to 3, hesperidin, a hesperidin derivative, and hesperetin; and
(b) at least a kind of xanthine derivatives, the mass ratio of (a):(b) in the composition being 1:(0.001 to 5).
[7] A composition for use for the prevention, amelioration, or treatment of metabolic syndrome, the composition comprising (a) and (b):
(a) at least a kind of polyphenols selected from the group consisting of a polyphenol containing 15 mass % or more of proanthocyanidin having a polymerization degree of 1 to 3, hesperidin, a hesperidin derivative, and hesperetin; and
(b) at least a kind of xanthine derivatives, the mass ratio of (a):(b) in the composition being 1:(0.001 to 5).
[8] Use of a composition comprising (a) and (b):
(a) at least a kind of polyphenols selected from the group consisting of a polyphenol containing 15 mass % or more of proanthocyanidin having a polymerization degree of 1 to 3, hesperidin, a hesperidin derivative, and hesperetin; and
(b) at least a kind of xanthine derivatives, for the production of a medicine for the prevention, amelioration, or treatment of metabolic syndrome, the mass ratio of (a):(b) in the composition being 1:(0.001 to 5).

Advantageous Effects of Invention

The composition of the present invention has an effect of inhibiting body weight increase, visceral fat accumulation, subcutaneous fat accumulation, and increase in plasma triglyceride level, and therefore is useful as a medicine, a food or drink, or a feed for weight loss; prevention or amelioration of obesity; and also prevention, amelioration, or treatment of metabolic syndrome, such as diabetes, hypertriglyceridemia, hypercholesterolemia, and arteriosclerosis, which are considered to result from visceral fat accumulation.

DESCRIPTION OF EMBODIMENTS

The present invention provides a composition for the prevention, amelioration, or treatment of metabolic syndrome, the composition comprising (a) and (b), wherein (a) is at least a kind of polyphenols selected from the group consisting of a polyphenol containing 15 mass % or more of proanthocyanidin having a polymerization degree of 1 to 3, hesperidin, a hesperidin derivative, and hesperetin; and
(b) is at least a kind of xanthine derivatives, the mass ratio of (b) to 1 part of (a) being 0.001 to 5 parts.

Hesperidin is a kind of polyphenol found abundantly in the skin of citrus fruits, such as mandarin oranges, and is also called vitamin P. Hesperidin is a hesperetin glycoside, and hesperetin is an aglycon of hesperidin. Examples of hesperidin derivatives include those prepared by addition of a methyl group, an ethyl group, a saccharide, or the like to hesperidin. Examples of hesperidin derivatives having a saccharide include, for example, a glucosyl hesperidin prepared by adding, to hesperidin, one or more kinds of saccharides, such as glucose, fructose, galactose, and xylose, in an equimolar or excess amount with use of a glycosyltransferase. Glucosyl hesperidins can be preferably used in the composition of the present invention because they are excellent in water solubility, processability into food or the like, bioabsorbability, etc. Among glucosyl hesperidins, alpha-glycosyl hesperidin, in which D-glucose residues in an equimolar or excess amount are bound to hesperidin by alpha bonds, is preferred.

Proanthocyanidin means a group of polyphenol compounds that produce anthocyanidin when treated with an acid, and is a generic term that includes flavan-3-ols (also referred to as catechins); and polymeric procyanidins, prodelphinidins, propelargonidins, and the like which are dimers, trimers, tetramers, and decamers or higher order polymers of flavan-3-ol esterified with gallic acid; and stereoisomers thereof. Proanthocyanidin is known to exist in various plants. Examples of plants containing proanthocyanidin include fruit vegetables, such as astringent persimmons, bananas, apples, pears, grapes, strawberries, avocados, cowberries, hawthorn apples, lotus roots, buckwheat, litchee nuts, and *Myrica rubra*; herbs and spices; wood; cinnamon; and pine bark.

In the composition of the present invention, the polyphenol containing 15 mass % or more of proanthocyanidin having a polymerization degree of 1 to 3, which is used as the component (a), needs to contain 15 mass % or more of proanthocyanidin having a polymerization degree of 1 to 3, and preferably 20 mass % or more, more preferably 25 mass % or more, further more preferably 30 mass % or more, and particularly preferably 35 mass % or more of such a proanthocyanidin. The more proanthocyanidin having a polymerization degree of 1 to 3 is contained, the more preferable the polyphenol is because of its higher bioabsorbability.

The content of proanthocyanidin having a polymerization degree of 1 to 3 in the polyphenol can be determined by a publicly known measuring method, such as HPLC. As a method for increasing the content of proanthocyanidin having a polymerization degree of 1 to 3 in the polyphenol, for example, a method of discarding polyphenol portions other than proanthocyanidin having a polymerization degree of 1 to 3, or a method of decomposing proanthocyanidin having a polymerization degree of 4 or more into low molecules (see, for example, WO 2006/090830) can preferably be used.

A composition containing a polyphenol containing 15% or more of proanthocyanidin having a polymerization degree of 1 to 3 is commercially available (for example, Oligonol (trade name), AMINO UP CHEMICAL Co., Ltd.), and such a product can also be preferably used as the component (a) of the present invention.

The component (a) may be any one kind, or a combination of two or more kinds selected from a polyphenol containing 15 mass % or more of proanthocyanidin having a polymerization degree of 1 to 3, hesperidin, a hesperidin derivative, and hesperetin.

Examples of the xanthine derivatives include xanthin, aminophylline, theophylline, cholinetheophylline, caffeine, theobromine, 1,7-dimethylxanthin, oxtriphylline, diprophylline, and proxyphylline. Inter alia, caffeine, theophylline, and theobromine are preferred.

The component (b) may be any one kind, or a combination of two or more kinds in combination of the xanthine derivatives exemplified above.

The blending ratio (mass ratio) of the component (a) and component (b) in the composition of the present invention is not particularly limited as long as the desired effects of the present invention can be achieved, but the mass ratio of (a):(b) is preferably about 1:(0.001 to 5), more preferably about 1:(0.01 to 0.5), and still more preferably about 1:(0.02 to 0.3).

The composition of the present invention has been confirmed to have an effect of inhibiting body weight increase, visceral fat accumulation, subcutaneous fat accumulation, and increase in plasma triglyceride level (see Test Examples 1 to 3), and therefore can be preferably used for the prevention, amelioration, or treatment of metabolic syndrome. The components (a) and (b) in the composition of the present invention, which are each already known to be useful when used alone for improving lipid metabolism or the like, are very useful when used in combination with each other, in that they exhibit a much stronger effect than in the cases where they are used alone, and that they produce a prominent effect even at low doses at which they separately cannot work (see Test Examples 1 to 3).

The composition of the present invention can be used as a medicine, a food or drink, a feed, a food additive, a feed additive, or the like. The composition is particularly preferable for use in a medicine, a food or drink, or a feed.

A medicine comprising the composition of the present invention may be orally or parenterally administered to a mammal. Examples of oral preparations include a granule, a powder, a tablet (including a sugar-coated tablet), a pill, a capsule, a syrup, an emulsion, and a suspension. Examples of parenteral preparations include injections (for example, a subcutaneous injection, an intravenous injection, an intramuscular injection, and an intraperitoneal injection), an intravenous fluid, external preparations (for example, an intranasal preparation, a transdermal preparation, and an ointment), and suppositories (for example, an intrarectal suppository and an intravaginal suppository). These preparations can be formulated with use of a pharmaceutically acceptable carrier by a method conventionally used in the art. Examples of the pharmaceutically acceptable carrier include an excipient, a binder, a diluent, an additive, a flavor, a buffer, a thickener, a colorant, a stabilizer, an emulsifier, a dispersant, a suspending agent, a preservative, and the like. For example, magnesium carbonate, magnesium stearate, talc, sugar, lactose, pectin, dextrin, starch, gelatin, tragacanth, methylcellulose, sodium carboxymethylcellulose, low-melting-point wax, cacao butter, or the like can be used as the carrier.

Oral solid preparations (a tablet, a pill, a capsule, a powder, a granule, or the like) can be formulated by conventional means including mixing an active ingredient with an excipient (lactose, mannitol, glucose, microcrystalline cellulose, starch, or the like), a binder (hydroxypropylcellulose, polyvinyl pyrrolidone, magnesium aluminometasilicate, or the like), a disintegrant (calcium cellulose glycolate, or the like), a lubricant (magnesium stearate, or the like), a stabilizer, a solubilizer (glutamic acid, aspartic acid, or the like), or the like. As needed, such preparations may be coated with a coating agent (saccharose, gelatin, hydroxypropylcellulose, hydroxypropyl methylcellulose phthalate, or the like), and the coating may consists of 2 or more layers.

Oral liquid preparations (a potus, a suspension, an emulsion, a syrup, an elixir, or the like) are formulated by dissolving, suspending, or emulsifying an active ingredient in a generally used diluent (purified water, ethanol, or the mixture thereof, or the like). The liquid preparation may further comprise a wetting agent, a suspending agent, an emulsifier, a sweetener, a flavor, an essence, a preservative, a buffer, or the like.

Injections include a solution, a suspension, an emulsion, and a solid injection to be dissolved or suspended in a solvent before use. Injections are formulated by dissolving, suspending, or emulsifying an active ingredient in a solvent. As the solvent, for example, distilled water for injection; physiological saline; a vegetable oil; alcohols, such as propylene glycol, polyethylene glycol, and ethanol; and a combination thereof may be used. The injection may further comprise a stabilizer, a solubilizer (glutamic acid, aspartic acid, Polysorbate 80 (registered trademark), or the like), a suspending agent, an emulsifier, a soothing agent, a buffer, a preservative, or the like. These injections are sterilized in the final step or produced by aseptic manipulation. The injection may be produced in a form of a sterile solid preparation, for example a lyophilized product, which can be dissolved in sterilized or sterile distilled water for injection or in another sterilized or sterile solvent just before use.

To a food or drink comprising the composition of the present invention, food additives generally used in a food or drink may be added, and the examples thereof include a sweetener, a colorant, a preservative, a thickener, an antioxidant, a color improver, a decolorant, an antifungal agent, a gum base, a bittering agent, an enzyme, a brightener, an acidulant, a seasoning, an emulsifier, a fortifier, a processing aid, a flavor, a spice extract, etc. The food or drink includes a health food, a functional food, a food for specified health use, and a food for the sick.

The food or drink suitable for the present invention is not particularly limited. Specific examples thereof include so-called dietary supplements, such as a tablet, a granule, a powder, and a health drink. Other examples include drinks, such as tea drink, refreshing drink, soda, nutritional drink, fruit juice, and lactic drink; noodles, such as buckwheat noodle, wheat noodle, Chinese noodle, and instant noodle; sweets and bakery products, such as candy, candy, gum, chocolate, snack, biscuit, jelly, jam, cream, baked goods, and bread; fishery or livestock products, such as fish sausage, ham, and sausage; dairy products, such as processed milk and fermented milk; fats, oils, and processed foods thereof, such as salad oil, oil for frying, margarine, mayonnaise, shortening, whipped cream, and dressing; seasonings, such as sauce and dipping sauce; retort pouch foods, such as curry, stew, sauce for rice-bowl cuisine, porridge, and rice soup; and frozen desserts, such as ice cream, sherbet, and shaved ice.

In light of the effects of the composition of the present invention, a food or drink prepared with use of the composition may be labeled as improving lipid metabolism; promoting basal metabolism; reducing body weight; reducing visceral fat or subcutaneous fat; having a slimming effect; preventing or treating obesity, or ameliorating a symptom thereof; and/or preventing or treating metabolic syndrome, or ameliorating a symptom thereof.

Examples of the feed comprising the composition of the present invention include a feed for livestock such as a cow, a horse, and a pig; a feed for poultry such as a chicken; and a feed for pet animals, such as a dog and a cat. The production of the feed of the present invention needs addition of the composition of the present invention, but other than that, the feed can be produced by an ordinary feed production method.

The amount of administration or intake of the medicine or the food or drink of the present invention may be determined depending on the age and body weight of the patient or ingester, symptoms, the administration time, the dosage form, the administration method, the combination of medicines, or the like. For example, preferred is that administration or intake is performed so that 0.05 to 3.0 g, preferably 0.2 to 1.0 g of the component (a) and 0.01 to 0.5 g, preferably 0.05 to 0.3 g of the component (b) are daily given to an adult human. Such a daily amount may be given in a single dose or in several divided doses.

EXAMPLES

Hereinafter, the present invention will be illustrated in more detail by Examples and Test Examples, but the present invention is not limited thereto.

Example 1

Powder

Powder ingredients, namely, glucosyl hesperidin (0.2 g), caffeine (0.02 g), vitamin C (0.28 g), synthetic aluminum silicate (10 g), potassium hydrogenphosphate (5 g), and lactose (84.5 g) were mixed uniformly to give a powder.

Example 2

Granule

Powder ingredients, namely, glucosyl hesperidin (0.2 g), caffeine (0.02 g), vitamin C (0.28 g), crystalline cellulose (40.0 g), lactose (35.0 g), starch (19.5 g), and polyvinyl alcohol (5.0 g), and water (30.0 g) were kneaded uniformly, ground and granulated, and then dried to give a granule.

Example 3

Tablet

With 99 g of the granule obtained in Example 2, 1 g of calcium stearate was mixed, and the mixture was compressed with use of a tableting machine to give tablets 6.0 mm in diameter.

Example 4

Blended Tea

Extraction from 1 g of a blend of 7 kinds of dried tea leaves, namely, green tea leaves, Job's tears, barley, brown rice, oolong tea leaves, Houttuynia *cordata* leaves, and Eucommia ulmoides leaves was performed with 100 mL of water. With the extract, glucosyl hesperidin (100 mg), caffeine (10 mg including 2 mg of ingredient-derived caffeine) and vitamin C (15 mg) were blended to give a blended tea.

Example 5

Powdered Tea

Brown rice tea extract (1800 mg), lactose (500 mg), citric acid (500 mg), glucosyl hesperidin (550 mg), and caffeine (55 mg including 20 mg of ingredient-derived caffeine) were blended to give a powdered tea.

Example 6

Candy

Glucosyl hesperidin (200 mg), caffeine (20 mg), citric acid (100 mg), vitamin C (15 mg), starch syrup (65 g), sucrose (10g), maleic acid (300 mg), succinic acid (200 mg), malic acid (150 mg), a flavor (0.3 g), and a small amount of water were mixed, and then heated and cooled in a conventional method to produce candies.

Test Example 1

When diet-induced obese mice were placed in a situation where caloric intake is controlled and they need to decompose and use body fat, decomposition and use of body fat is promoted, ameliorating obesity. In such a situation, the effect of the composition of the present invention comprising glucosyl hesperidin and caffeine was investigated. As the glucosyl hesperidin and caffeine, "Hayashibara Hesperidin S (trade name)" (distributor: Hayashibara Co., Ltd.) and "Chanomoto (trade name)" (purity of caffeine: 98.5%, made by Shiratori Pharmaceutical Co., Ltd.) were used, respectively.

Five-week-old male KK mice were fed with water and a powder feed for breeding (CE-2 (trade name), made by CLEA Japan, Inc.) for one week, and then fed with the high-calorie feed (4.70 kcal/g) in Table 1 shown below for 3 weeks for induction of obesity. The mice were divided into 4 groups (a control group, a caffeine administration group, a glucosyl hesperidin administration group, and a present invention administration group (caffeine+glucosyl hesperidin), 5 to 8 mice per group) and fed with the low-calorie feed (3.16 kcal/g) in Table 1 shown below or the low-calorie feed supplemented with the corresponding test sample for 2 weeks, in expectation of using body fat. The feeds given to the test groups are as follows.

(1) Control group; low-calorie feed
(2) Caffeine administration group; low-calorie feed+0.025 mass % of caffeine
(3) Glucosyl hesperidin administration group; low-calorie feed+0.25 mass % of glucosyl hesperidin
(4) Present invention (mixture of glucosyl hesperidin and caffeine (10:1)) administration group; low-calorie feed+ (0.25 mass % of glucosyl hesperidin+0.025 mass % of caffeine)

TABLE 1

Compositions of high-calorie feed and low-calorie feed

| Composition | High-calorie feed | (Unit: mass %) Low-calorie feed |
|---|---|---|
| Cornstarch | 53.25 | 53.25 |
| Casein | 18.00 | 18.00 |
| Corn oil | 20.00 | 2.50 |
| Cellulose | 2.50 | 20.00 |
| AIN93G Mineral Mix[1] | 5.00 | 5.00 |

TABLE 1-continued

Compositions of high-calorie feed and low-calorie feed

| Composition | High-calorie feed | (Unit: mass %) Low-calorie feed |
|---|---|---|
| AIN93 Vitamin Mix[1] | 1.00 | 1.00 |
| Choline bitartrate | 0.25 | 0.25 |
| Calorie (kcal/g) | 4.73 | 3.16 |

[1]Made by Oriental Yeast Co., Ltd.

During the test period (2 weeks from the start of low-calorie feeding), body weight and feed intake were periodically measured. After the end of the test, the mice were euthanized, and mesenteric (visceral) fat tissue was removed and weighed.

Figure 1:
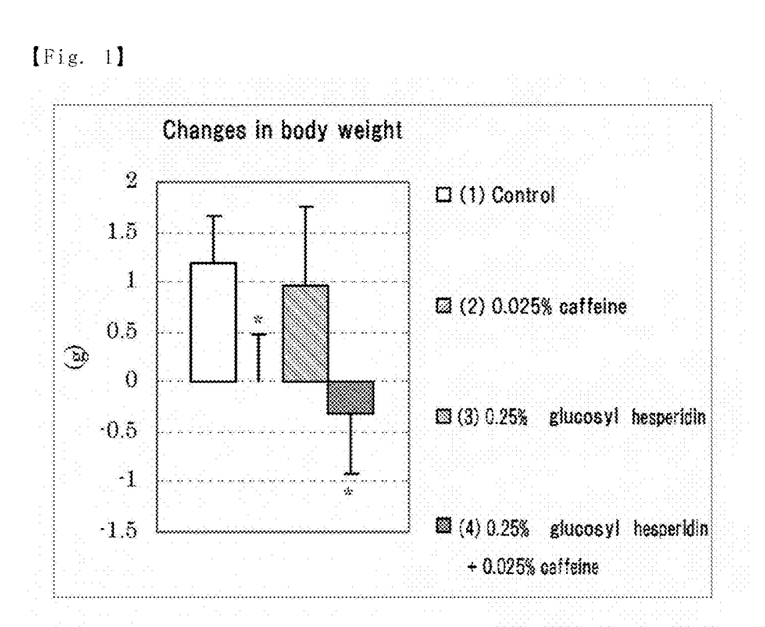
FIG. 1 is a graph showing the changes in body weight before and after the test period in Test Example 1.
Figure 2:
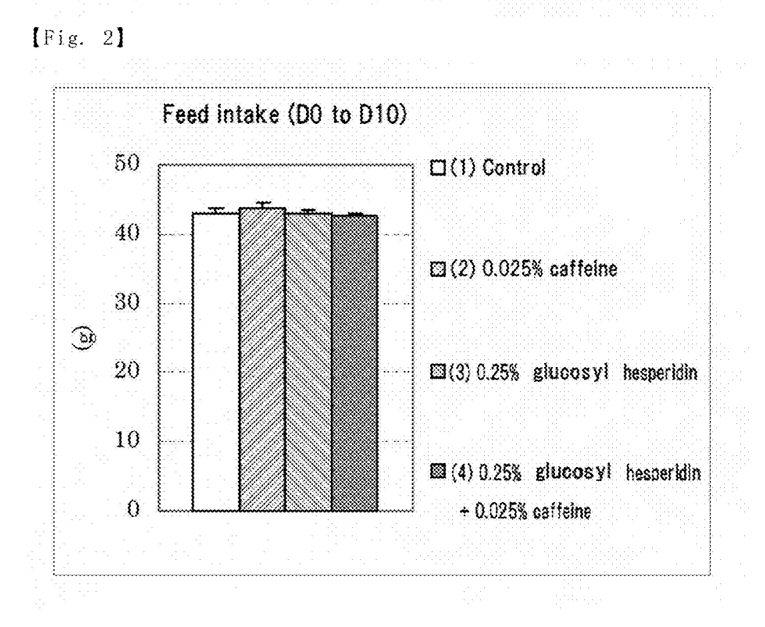
FIG. 2 is a graph showing the feed intake during the first 10 days of the test period in Test Example 1.
Figure 3:
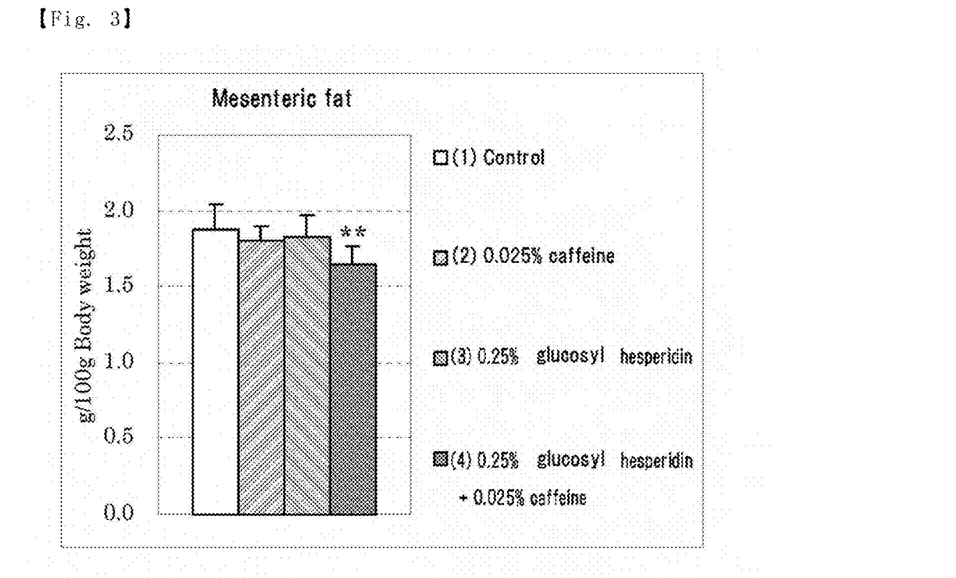
FIG. 3 is a graph showing the weight of mesenteric fat tissue per 100 g of body weight in Test Example 1.

The changes in body weight before and after the test period is shown in FIG. 1, the feed intake during the first 10 days of the test period is shown in FIG. 2, and the weight of mesenteric fat tissue per 100 g of body weight is shown in FIG. 3. The results are shown as Mean±SD of each group. The ** and * in the figures indicate a significant difference with a risk less than 1% and a risk less than 5% from the control, respectively.

These results show the following. Regarding the weight of mesenteric (visceral) fat tissue, while the caffeine administration group and the glucosyl hesperidin administration group did not show any significant difference as compared with the control group, the present invention administration group showed significantly lower values, i.e., a clear synergistic effect. Also, regarding the changes in body weight, as compared with the control group, the caffeine administration group showed significantly lower values, but the glucosyl hesperidin administration group showed equivalent values. Meanwhile, the present invention administration group showed significantly lower values, which were even lower than those of the caffeine administration group, i.e., a clear synergistic effect. These results showed that the composition of the present invention comprising glucosyl hesperidin and caffeine, due to the clear synergistic effect of reducing body weight and visceral fat, is useful for the prevention or amelioration of metabolic syndrome.

Test Example 2

Under the same conditions as in Test Example 1, the effect of the composition of the present invention comprising glucosyl hesperidin and caffeine was investigated. The glucosyl hesperidin and caffeine used here were the same as in Test Example 1.

Five-week-old male KK mice were fed with water and a powder feed for breeding (CE-2 (trade name), made by CLEA Japan, Inc.) for one week, and then fed with the high-calorie feed (4.70 kcal/g) in Table 1 for 3 weeks for induction of obesity. The mice were divided into 6 groups (a control group, a caffeine administration group, a glucosyl hesperidin administration group, and mixture of caffeine and glucosyl hesperidin (present invention) administration groups, 6 to 7 mice per group) and fed with the low-calorie feed (3.16 kcal/g) in Table 1 or the low-calorie feed supplemented with the corresponding test sample for 2 weeks, in expectation of using body fat. The feeds given to the test groups are as follows.

(1) Control group; low-calorie feed
(2) Caffeine administration group; low-calorie feed+0.0125 mass % of caffeine
(3) Glucosyl hesperidin administration group; low-calorie feed+0.25 mass % of glucosyl hesperidin (4) Mixture of glucosyl hesperidin and caffeine (10:1) administration group; low-calorie feed+(0.25 mass % of glucosyl hesperidin+0.025 mass % of caffeine)
(5) Mixture of glucosyl hesperidin and caffeine (20:1) administration group; low-calorie feed+(0.25 mass % of glucosyl hesperidin+0.0125 mass % of caffeine)
(6) Mixture of glucosyl hesperidin and caffeine (40:1) administration group; low-calorie feed+(0.25 mass % of glucosyl hesperidin+0.00625 mass % of caffeine)

During the test period (2 weeks from the start of low-calorie feeding), body weight and feed intake were periodically measured. After the end of the test, the mice were euthanized, and subcutaneous fat tissue and mesenteric (visceral) fat tissue were removed and separately weighed.

Figure 4:
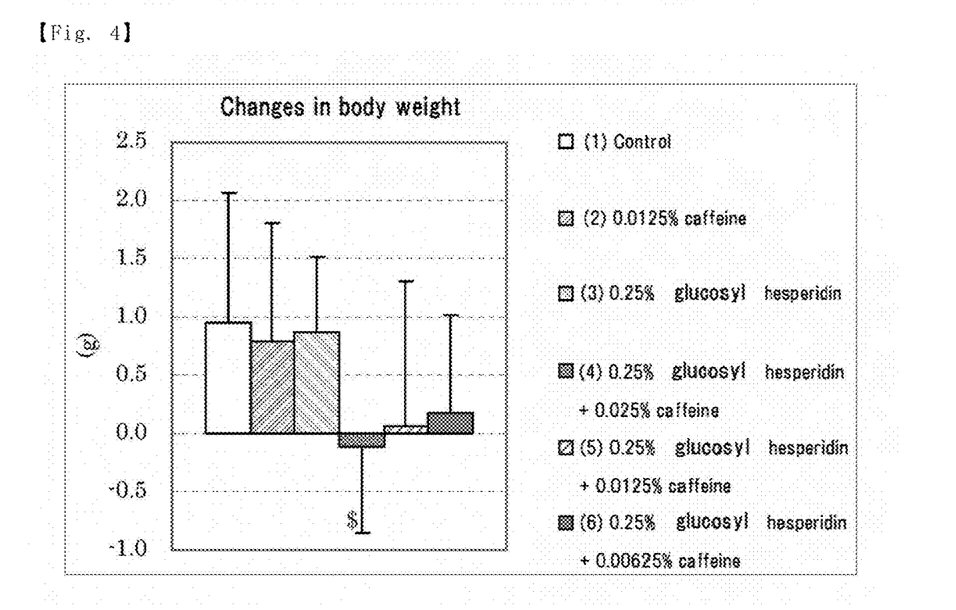
FIG. 4 is a graph showing the changes in body weight before and after the test period in Test Example 2.
Figure 5:
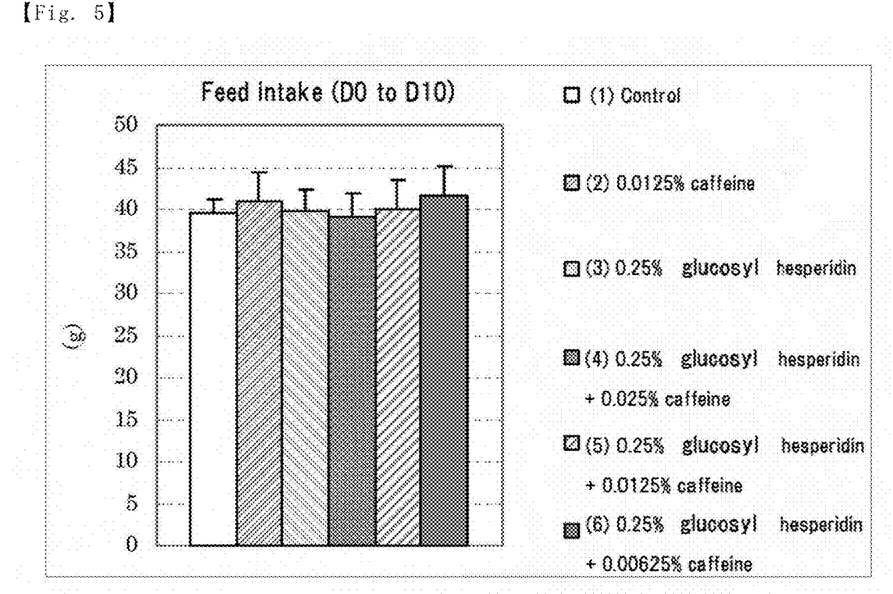
FIG. 5 is a graph showing the feed intake during the first 10 days of the test period in Test Example 2.
Figure 6:
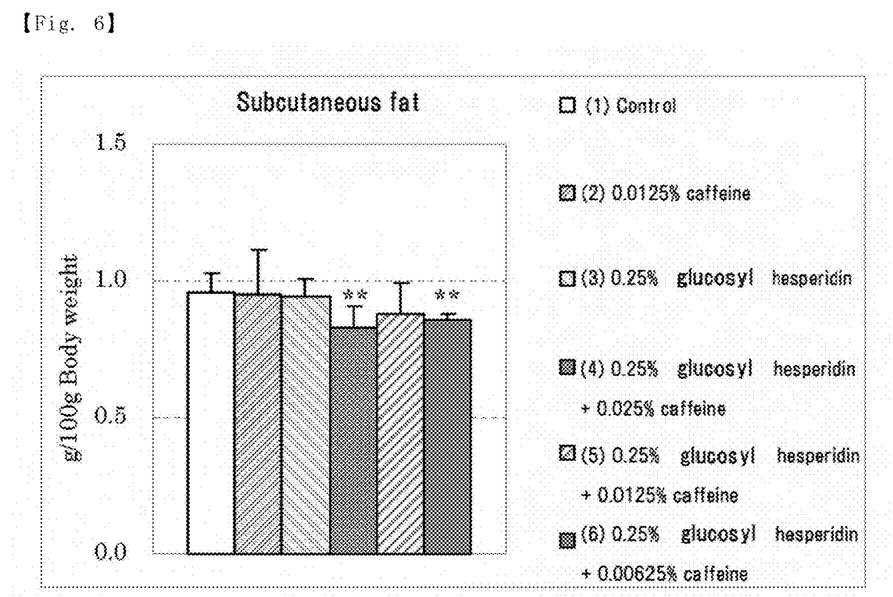
FIG. 6 is a graph showing the weight of subcutaneous fat tissue per 100 g of body weight in Test Example 2.
Figure 7:
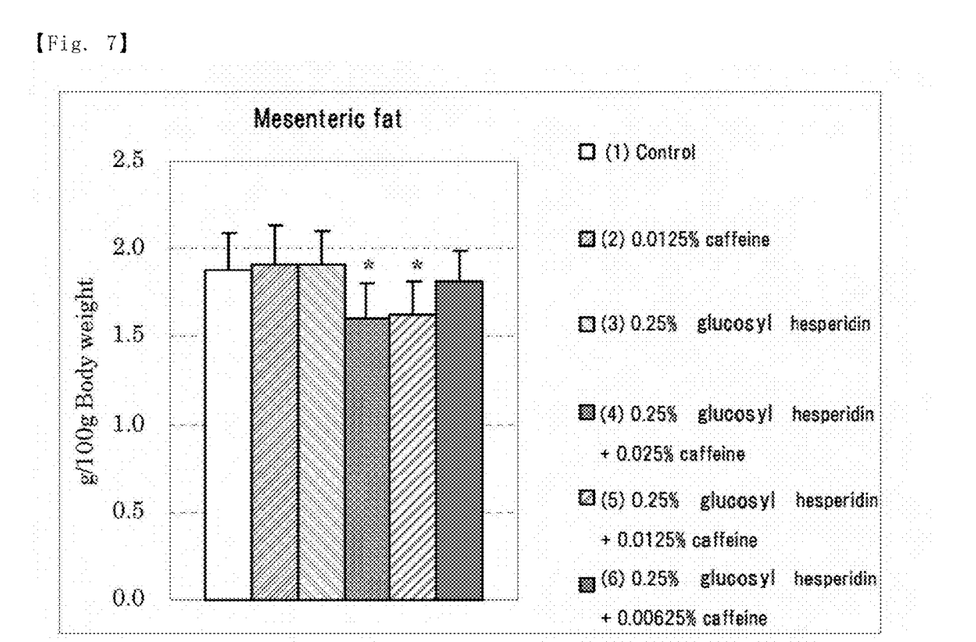
FIG. 7 is a graph showing the weight of mesenteric fat tissue per 100 g of body weight in Test Example 2.

The changes in body weight before and after the test period is shown in FIG. 4, the feed intake during the first 10 days of the test period is shown in FIG. 5, the weight of subcutaneous fat tissue per 100 g of body weight is shown in FIG. 6, and the weight of mesenteric fat tissue per 100 g of body weight is shown in FIG. 7. The results are shown as Mean±SD of each group. The $, **, and * in the figures indicate a significant difference with a risk less than 10%, a risk less than 1%, and a risk less than 5% from the control, respectively.

These results show the following. Regarding the weight of mesenteric (visceral) fat tissue and the weight of subcutaneous fat tissue, while the caffeine administration group and the glucosyl hesperidin administration group did not show any significant difference as compared with the control group, the present invention (mixture of glucosyl hesperidin and caffeine) administration groups showed significantly lower values, i.e., a clear synergistic effect. Also, regarding the changes in body weight, the caffeine administration group and the glucosyl hesperidin administration group showed values equivalent to those of the control group. Meanwhile, the present invention (mixture of glucosyl hesperidin and caffeine) administration groups showed lower values, i.e., a clear synergistic effect. These results showed that the composition of the present invention comprising glucosyl hesperidin and caffeine, due to the clear synergistic effect of reducing body weight, visceral fat accumulation, and subcutaneous fat accumulation, is useful for the prevention or amelioration of metabolic syndrome.

Test Example 3

Under the same conditions as in Test Example 1, the effect of the composition of the present invention comprising a polyphenol containing 15 mass % or more of proanthocyanidin having a polymerization degree of 1 to 3 and caffeine was investigated. As the polyphenol containing 15 mass % or more of proanthocyanidin having a polymerization degree of 1 to 3 and caffeine, "Oligonol (trade name)" (distributor: AMINO UP CHEMICAL Co., Ltd.) and "Chanomoto (trade name)" (purity of caffeine: 98.5%, made by Shiratori Pharmaceutical Co., Ltd.) were used, respectively.

Five-week-old male KK mice were fed with water and a powder feed for breeding (CE-2 (trade name), made by CLEA Japan, Inc.) for one week, and then fed with the high-calorie feed (4.70 kcal/g) in Table 1 for 3 weeks for induction of obesity. The mice were divided into 4 groups (a control group, a caffeine administration group, an Oligonol administration group, and a present invention administration group (Oligonol+caffeine), 5 to 8 mice per group) and fed with the low-calorie feed (3.16 kcal/g) in Table 1 or the low-calorie feed supplemented with the corresponding test sample for 2 weeks, in expectation of using body fat. The feeds given to the test groups are as follows.

(1) Control group; low-calorie feed
(2) Caffeine administration group; low-calorie feed+0.025 mass % of caffeine
(3) Oligonol administration group; low-calorie feed+0.1 mass % of Oligonol
(4) Present invention (mixture of Oligonol and caffeine (4:1)) administration group; low-calorie feed+(0.1 mass % of Oligonol+0.025 mass % of caffeine)

During the test period (2 weeks from the start of low-calorie feeding), body weight and feed intake were periodically measured. After the end of the test, the mice were euthanized, and subcutaneous fat tissue, epididymal fat tissue, and mesenteric (visceral) fat tissue were removed and separately weighed. Also, at the start of the test period (the start of low-calorie feeding) and the end of the test period, plasma triglyceride level was measured.

Figure 8:
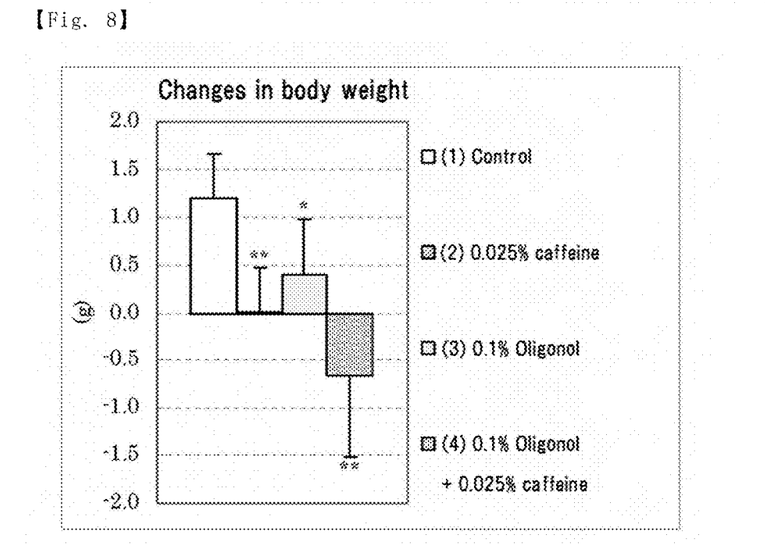
FIG. 8 is a graph showing the changes in body weight before and after the test period in Test Example 3.
Figure 9:
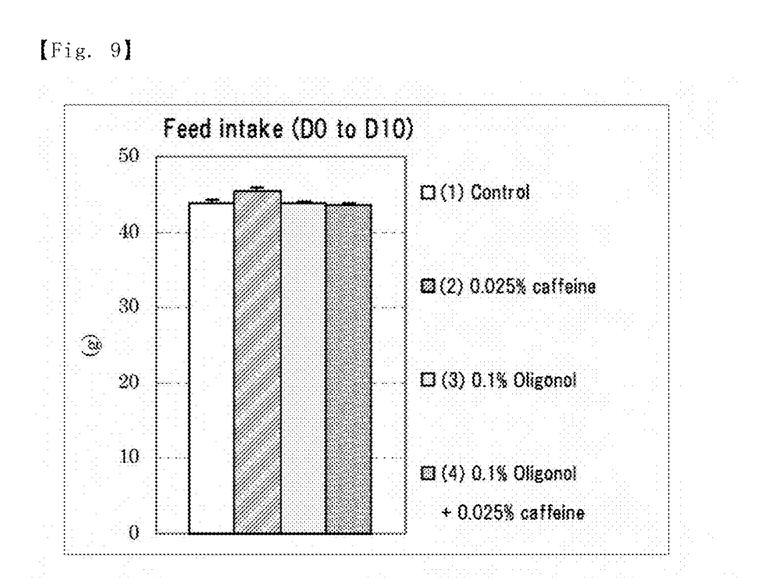
FIG. 9 is a graph showing the feed intake during the first 10 days of the test period in Test Example 3.
Figure 10:
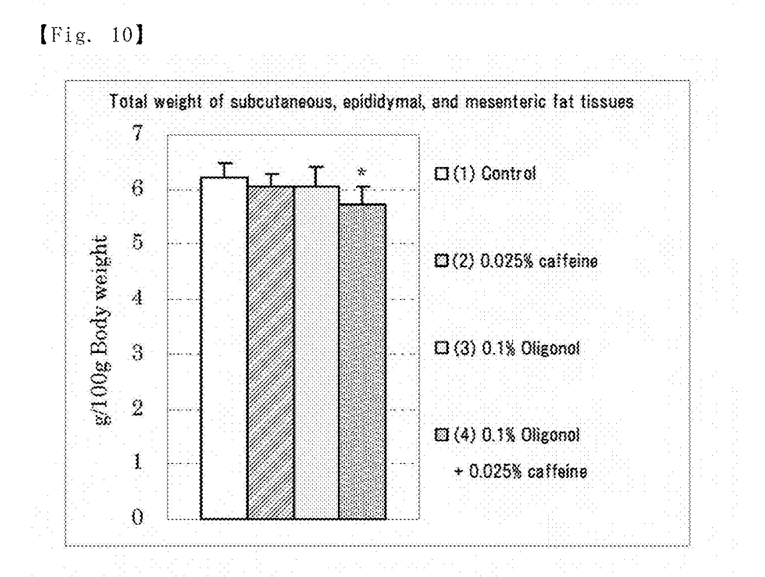
FIG. 10 is a graph showing the total weight of subcutaneous, epididymal, and mesenteric fat tissues per 100 g of body weight in Test Example 3.
Figure 11:
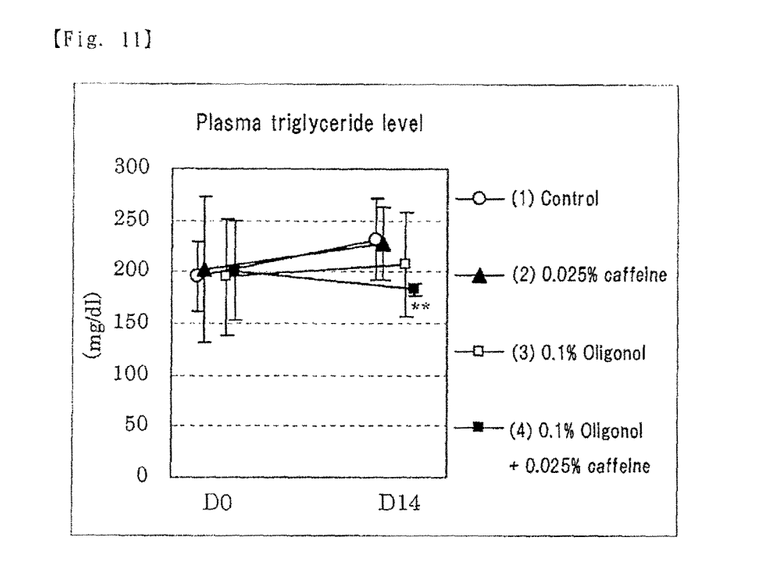
FIG. 11 is a graph showing the changes in plasma triglyceride level before and after the test period.

The changes in body weight before and after the test period is shown in FIG. 8, the feed intake during the first 10 days of the test period is shown in FIG. 9, the total weight of subcutaneous, epididymal, and mesenteric fat tissues per 100 g of body weight is shown in FIG. 10, and the changes in plasma triglyceride level before and after the test period is shown in FIG. 11. The results are shown as Mean±SD of each group. The ** and * in the figures indicate a significant difference with a risk less than 1% and a risk less than 5% from the control, respectively.

These results show the following. Regarding the total weight of fat tissues, while the caffeine administration group and the Oligonol administration group did not show any significant difference as compared with the control group, the present invention administration group showed significantly lower values, i.e., a clear synergistic effect. Regarding the changes in body weight, while the caffeine administration group and the Oligonol administration group showed lower values as compared with the control group, the present invention administration group showed even lower values, i.e., a clear synergistic effect. Further, regarding the values of plasma triglyceride level measured on the 14th day, while the caffeine administration group and the Oligonol administration group did not show any significant difference as compared with the control group, the present invention administration group showed significantly lower values, i.e., a clear synergistic effect. These results showed that the composition of the present invention comprising Oligonol and caffeine, due to the clear synergistic effect of reducing body weight, visceral fat accumulation, and subcutaneous fat accumulation, and of inhibiting increase in plasma triglyceride level, is useful for the prevention, amelioration, or treatment of metabolic syndrome.

The invention claimed is:

1. A method for the amelioration, or treatment of metabolic syndrome in a subject suffering therefrom comprising administering to said subject a composition comprising (a) and (b):
    (a) at least one kind of polyphenols selected from the group consisting of hesperidin and glucosyl hesperidin; and
    (b) caffeine, the mass ratio of (a):(b) in the composition being 1 :(0.025 to 0.1).

2. A method for the amelioration or treatment of metabolic syndrome, comprising administering a medicine, a food or drink, or a feed comprising the composition defined in claim 1.

* * * * *